United States Patent
Headley

(10) Patent No.: US 9,585,809 B2
(45) Date of Patent: Mar. 7, 2017

(54) WRIST BAND MOTION ANALYZER WITH COMPARISON FEEDBACK

(71) Applicant: Aaron Headley, Plano, TX (US)

(72) Inventor: Aaron Headley, Plano, TX (US)

( * ) Notice: Subject to any disclaimer, the term of this patent is extended or adjusted under 35 U.S.C. 154(b) by 742 days.

(21) Appl. No.: 13/929,613

(22) Filed: Jun. 27, 2013

(65) Prior Publication Data

US 2014/0066698 A1 Mar. 6, 2014

Related U.S. Application Data

(60) Provisional application No. 61/667,449, filed on Jul. 3, 2012.

(51) Int. Cl.
| | |
|---|---|
| *A61H 19/00* | (2006.01) |
| *G01P 5/00* | (2006.01) |
| *A61B 5/00* | (2006.01) |
| *A61H 37/00* | (2006.01) |

(52) U.S. Cl.
CPC ............ *A61H 19/34* (2013.01); *A61B 5/681* (2013.01); *A61H 19/50* (2013.01); *A61H 37/00* (2013.01); *A61H 19/40* (2013.01); *A61H 2201/5023* (2013.01); *A61H 2201/5061* (2013.01); *A61H 2201/5079* (2013.01); *A61H 2201/5084* (2013.01); *A61H 2201/5097* (2013.01)

(58) Field of Classification Search
CPC ........ A61H 19/40; A61H 19/44; A61H 19/50; A61H 2201/5058; A61H 2201/5061; A61H 2201/5076; A61H 2201/5084; A61H 2201/5079; G01C 21/10; G01C 21/16; G01D 21/02; G06F 19/3418; G06F 19/3443; A61B 5/3802; A61B 5/681; A61B 5/1118
USPC .................................................. 702/141, 41
See application file for complete search history.

(56) References Cited

U.S. PATENT DOCUMENTS

| | | | | |
|---|---|---|---|---|
| 8,092,393 | B1 * | 1/2012 | Rulkov | A61B 5/02438 600/301 |
| 8,112,281 | B2 * | 2/2012 | Yeung | G04C 3/002 704/270 |
| 8,172,761 | B1 * | 5/2012 | Rulkov | A61B 5/01 600/301 |
| 8,626,472 | B2 * | 1/2014 | Solinsky | A61B 5/112 702/141 |
| 8,957,785 | B1 * | 2/2015 | Matak | H04Q 9/00 340/870.07 |
| 2010/0250179 | A1 * | 9/2010 | Mariano | A63K 3/00 702/96 |

(Continued)

*Primary Examiner* — Matthew F Desanto

(57) ABSTRACT

The Wrist Band Motion Analyzer with Comparison Feedback is a wrist worn device that shows feedback to the user wearing the device in order to achieve the correct speed and force of the user's hand. The purpose of the Wrist Band Motion Analyzer is to give the user wearing the device real time feedback in order to achieve a specific speed and G-force of the wearers hand motion; whereas when accomplished may lead to the wearer's woman partner achieving an ejaculating orgasm with locked fingers placed correctly on the G-spot. This new device gives real time feedback to the proper speed and G-force of the user's hand compared to a pre-programmed G-force and frequency which is known to give women an ejaculating orgasm. This is achieved by measuring the G-force and speed in real time through the use of an accelerometer and microcontroller.

8 Claims, 3 Drawing Sheets

(56) References Cited

U.S. PATENT DOCUMENTS

| | | | | |
|---|---|---|---|---|
| 2011/0054782 A1* | 3/2011 | Kaahui | ................ | A61B 5/1107 |
| | | | | 701/532 |
| 2012/0088982 A1* | 4/2012 | Rulkov | .............. | A61B 5/02438 |
| | | | | 600/301 |
| 2013/0023781 A1* | 1/2013 | Freeman | ............... | A61B 5/0535 |
| | | | | 600/529 |
| 2013/0173171 A1* | 7/2013 | Drysdale | ............... | A61B 5/1118 |
| | | | | 702/19 |
| 2013/0332286 A1* | 12/2013 | Medelius | ................. | A61B 5/01 |
| | | | | 705/14.66 |

* cited by examiner

WRIST BAND MOTION ANALYZER WITH COMPARISON FEEDBACK

The Wrist Band Motion Analyzer is a wrist worn device that shows feedback to the wearer of the device in order to achieve a certain speed and force of the wear's hand motion. The intent of the Wrist Band Motion Analyzer is to match a correct force and speed of the hand motion that is pre-programmed into the device. This can be used to achieve a female ejaculating orgasm.

BACKGROUND OF THE INVENTION

1. Field of the Invention

The present invention relates generally to a device worn on the wrist providing real time measurement of the wrist speed; another embodiment of the device provides real time feedback of the force of a user's hand motion. The purpose of this device is to match the correct speed and force of the wrist motion in order to ensure female ejaculation.

2. Background

Currently there is no such wrist worn device which shows the correct G-force and speed of the wrist/hand/finger motion for the purpose of creating an ejaculating orgasm in women. There are instructions showing proper finger and hand placement on the G-spot for a desired result however there isn't a device assisting with the correct force and frequency (hand speed) only videos showing the general concept. There is a technique using ones fingers placed correctly on the G-spot of a women which if pressing repeatedly at a certain speed and force can create an ejaculating orgasm in women. It is difficult to achieve the correct finger/hand speed/frequency and force on the G-spot. This invention gives the user feedback to properly achieve that speed/frequency and G-force. Currently there is not a solution helping to address this problem of proper G-force and frequency of palpitations on a women's G-spot to cause an ejaculating orgasm. The odds of success by simply watching instructional videos is low. This device increases the user's success rate greatly.

It would be desirable to have a device with feedback worn on the hand-wrist-arm which gives feedback when achieving a known frequency and G-force which helps women achieve an ejaculating orgasm that uses a wrist worn device which gives real time feedback through red, yellow, and green light emitting diodes (LED's). This is showing starting speed red, a medium speed yellow, and green when the speed reaches the optimum speed/frequency of wrist motion. The same is shown on separate light emitting diodes red for beginning force yellow for mid range force and green once the optimum force is achieved. The proper feedback works whether the watch is worn on the top of the wrist or the bottom of the wrist. In general the device looks like a watch and is water resistant having a circuit board with LED's (Light emitting diodes) microprocessor and accelerometer behind a lens inside of a typical looking watch body which may function as a regular watch in disguise. A button is used to start and stop the device. The LED's blink quickly then shut off when turned on. They blink at a slower rate indicating when turned off. A wrist strap is used to ensure the device is snuggly attached to the wrist. This device can be used as feedback for the force of the user's wrist/hand motion with fingers placed against the G-spot of a woman to achieve an ejaculating orgasm. Therefore, there currently exists a need in the industry for a device that assists in the proper wrist hand/finger motion for helping achieve a women's ejaculating orgasms.

SUMMARY OF THE INVENTION

The present invention advantageously fills the aforementioned deficiencies by providing a wrist watch like device with feedback helping women achieve an ejaculating orgasm which provides feedback towards an optimum speed and force of the users' fingers and hand wrist action.

The end user must achieve a certain speed/frequency of hand motion as well as a certain force for each separate red yellow green light. Correct motion and force although independent will display both green lights when the optimum frequency and force is achieved at which point the woman will most likely achieve a G-spot orgasm with associated ejaculation.

Additional feedback features could be vibration at time of achieved speed and/or frequency of watch worn on wrist also Bluetooth RF feedback and or audio feedback. The device may be disguised as a watch showing proper time as well as typical normal wrist watch functions. This invention provides correct feedback regardless of body angle of hand wrist position and placement on the wrist by looking at the x, y, and z axis of the accelerometer data. Another possible form of desired feedback may be from a wireless audio device in the ear such as a Bluetooth headset. Optional sound feedback when frequency and G-force are reached. An additional feature is that the device goes to sleep after a certain time of inaction when not seeing the minimum level of force or frequency. The correct force and frequency is displayed as green LED's when compared to known correct force and frequency measurements taken from an expert in the industry compared against that data to know when the optimum speed and force are achieved which is shown by separate green light emitting diodes for speed and force. A wrist strap is used so that the device can be snuggly strapped to any size wrist so that there is no slop or play which could lead to an inaccurate reading. LED's are used so that feedback can be recognized in day or night lighting conditions and under extreme motion conditions looking like a red or yellow or green blur from two different sets of colored LED's.

This device makes it possible to create the correct G-force and speed of wrist to assist in the elusive female ejaculating orgasm. Separate video instruction of correct finger and hand placement is provided with the product.

This is a wrist worn device that looks like a watch with visual light feedback red yellow and green LED's. Two separate sets of LED's independently showing G-force and frequency/speed. Firmware running in a microprocessor collects the data from all three axis of the accelerometer continuously. Samples are averaged for accuracy to eliminate any noise or false readings. A Fast Fourier Transform is employed to properly compute the correct speed/frequency. An example would be a minimum starting speed would light the red LED. When a mid-frequency of wrist motion is reached red is turned off and the yellow LED is lit. When the optimum speed or greater is reached the green LED is lit, similar for the G-force set of LED's. When a certain minimum G-force is reached the red LED is lit. When the mid frequency of force is reached the yellow is lit and the red is turned off. When the optimum force is reached the green LED is lit and both red and yellow LED are off. The exact frequency and force numbers are proprietary based on the internal table of correct frequency and force based on several masters in the industry. These stored values are between 1 Hz and 20 Hz. The G-force is between 1 G and 12 G.

Among other things, it is an objective of the present invention to provide a Watch like wrist worn device with feedback assisting the user in achieving ejaculating orgasms in women that does not suffer from any of the problems or deficiencies associated with prior solutions.

This device coaches the user to use the correct speed and force of the hand fingers to properly achieve a female ejaculating orgasm. Once the correct speed and force is learned the user may be trained so that they no longer need the device once trained by the feedback from the device.

This device is battery powered, lasting as long as the shelf life of a typical watch battery when not in use. The device has been optimized for low energy consumption such that it will last for many sessions.

This device may also be attached to other powered machines designed for female pleasure so that proper speed and force can be obtained.

The present invention now will be described more fully hereinafter with reference to the accompanying drawings, which are intended to be read in conjunction with both this summary, the detailed description and any preferred and/or particular embodiments specifically discussed or otherwise disclosed. This invention may, however, be embodied in many different forms and should not be construed as limited to the embodiments set forth herein; rather, these embodiments are provided by way of illustration only and so that this disclosure will be thorough, complete and will fully convey the full scope of the invention to those skilled in the art.

DETAILED DESCRIPTION OF THE INVENTION

The present invention is directed to a wrist worn device with feedback helping the user create a G-Spot (Grafenberg Spot) orgasm in women which typically is accompanied by ejaculation or otherwise known as a squirting orgasm.

Figure 1:
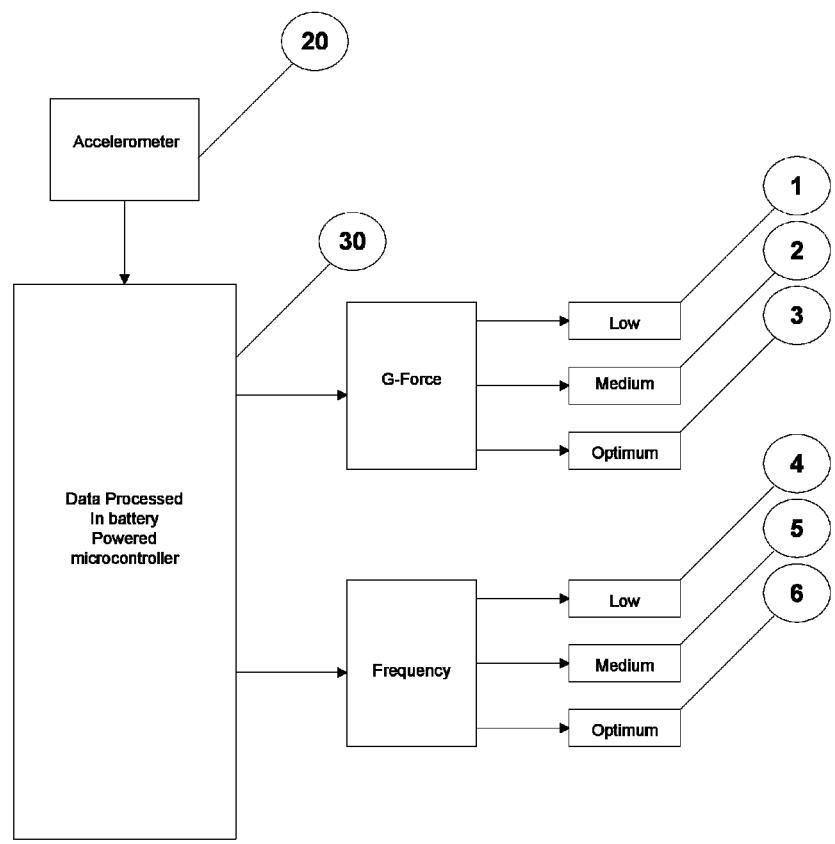
FIG. 1 shows the flow diagram of data coming into the device how it is processed and displayed in condensed form.
Figure 2:
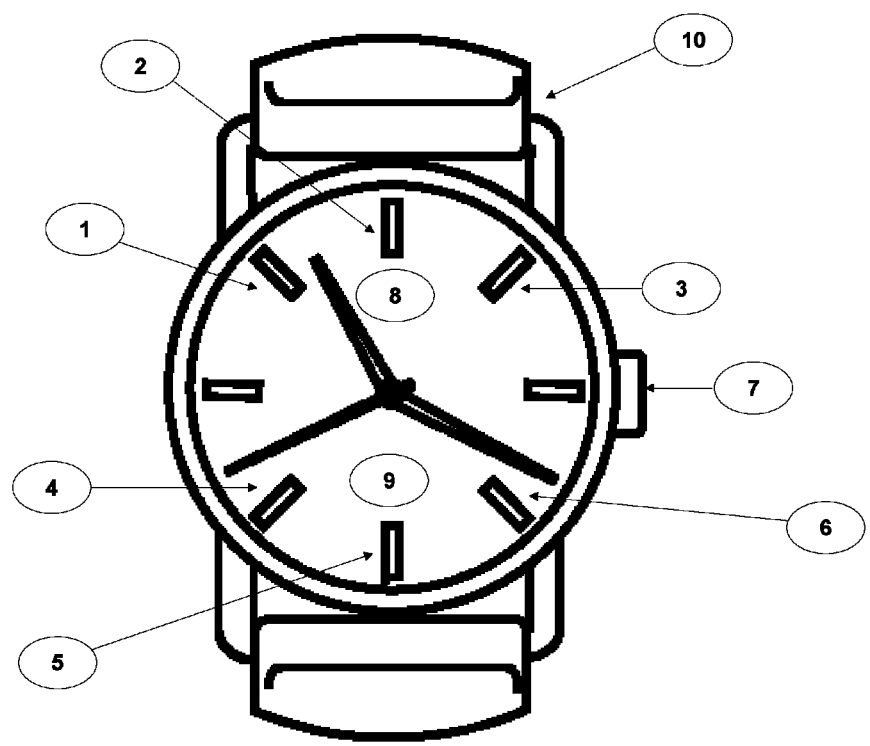
FIG. 2 shows a working prototype device with the Speed LEDs and G-force LEDs and watch like frame.

In its most complete version see FIG. 2, the system of the present invention is made up of the following components. There is a start button 7 which has been configured so that when the user pushes the button the device turns on. The microprocessor FIG. 1 30 starts the accelerometer 20 and takes data from it. This data is processed to find the G-force and frequency at any given moment that the accelerometer is experiencing. Through software this raw data is processed to acquire an average speed/frequency and G-force in real time. LEDs (Light Emitting Diodes) 1, 2, 3, 4, 5, and 6 as illustrated in FIGS. 1 and 2, give feedback on two separate scales. One set for the proper frequency/speed 9 of the wearer of the device and the other set of LEDs for the proper G-force 8 of the wearer of the devices wrist motion. For example when a certain minimum motion is detected the red LED is lit for low frequency 4. This is an indicator to the user that they need to increase the frequency of the wrist motion. In other words speed up the wrist/hand/finger motion. By doing this eventually a yellow LED will light 5 and the red will go off 4. Faster speed make the green LED come on 6 and both the yellow 5 and red 4 will be off indicating that the optimum speed has been reached. The same is true for the G-force indicators 1, 2, 3. Further examples are changes from red 4 to yellow 5 LED occurs on the speed scale when low to mid range frequency is achieved. Red 1 to yellow 2 LED color changes on the G-force LED scale when a certain mid G-force is achieved. Yellow 5 to green 6 LED is displayed on the speed/frequency scale when mid to optimal or greater speed/frequency is achieved. Yellow 2 to green 3 LED is changed on the G-force scale when mid G-force to optimum G-force is achieved. Both sets of Red Yellow and Green 1, 2, 3, 4, 5, 6 LED's function independently. Various capacitors and resistors are used to limit current to the LED's and achieve proper function of the accelerometer 20 and microcontroller 30. The system is powered from a single battery although in the case of a disguised watch, the watch may run from an independent battery. The mechanical package is very similar in nature to a wrist worn watch with lens, push button 7, wrist band 10 and is also water proof to at least 1 meter or greater by use of a compressed rubber gasket. These components are combined together to create an architecture for the system that has real time averaged feedback of G-force and frequency of human wrist motion reaching a desired Green lit LED for both frequency 6 and separate G-force 3 compared to a known successful set of data which when moved in motion on the wrist with proper hand finger placement on the G-spot in a woman will most likely achieve a G-spot orgasm for that woman. It should further be noted that: typically women ejaculate at this point known as a squirting orgasm. The watch like worn device will employ a snug fully adjustable wrist strap 10 for snug fit on any user. The watch is made of typical industry plastics, metals, lens and seals for water proof/resistance use see FIG. 2 for a working physical example.

Figure 3:
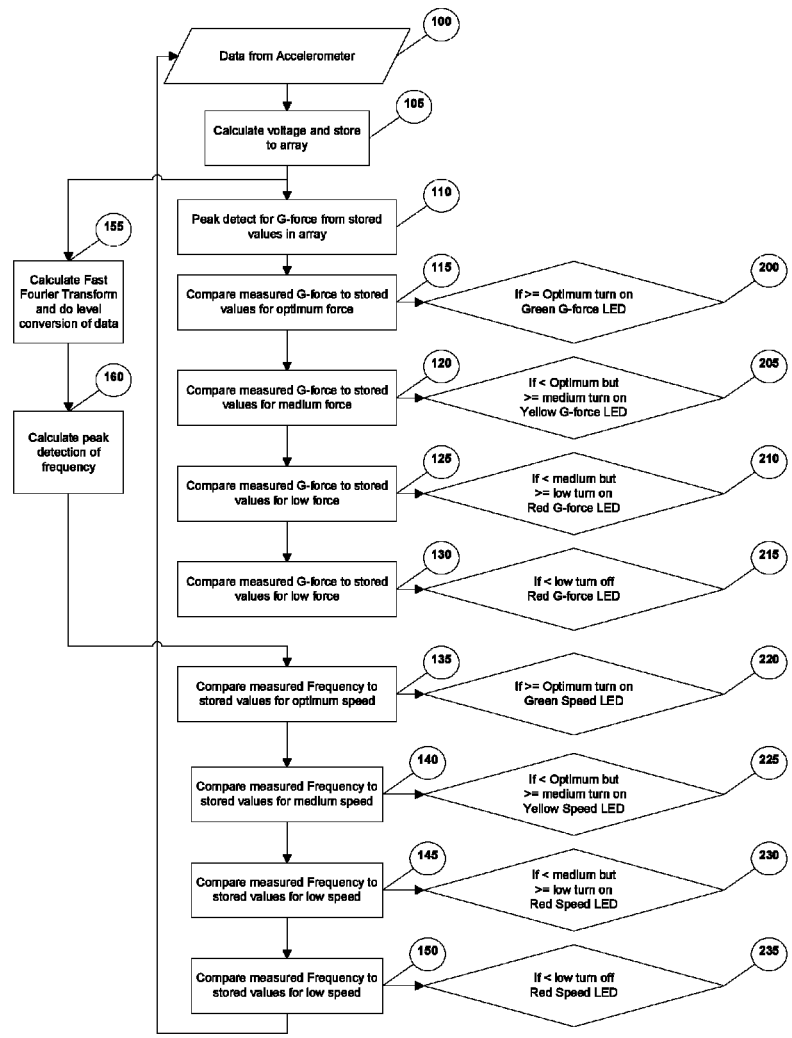
FIG. 3 shows the firmware block diagram.

With respect to the firmware, in its most complete and preferred version, it is made up of the following executable steps: See FIG. 3 for the flow chart.

The microcontroller 30 is woken by an interrupt when an external button 7 is pushed on the watch. Multiple data points are read 105 from the accelerometer 20, 100 and averaged 155, 160 to eliminate false or noisy sample readings. This gives an accurate G-force and frequency/speed data measurement. Once averaged it is compared against an expert set of data 110, 115, 120, 125, 130, 135, 140, 145, 150. If too low 210,215, 230,235 a Red LED 1, 4 is lit. If mid-range is reached 205, 225 a yellow LED 2, 5 is lit. If equal or greater in G-force 200 a green LED 3 is lit.

If equal or greater for speed 220 a green LED 6 is lit. The device starts out with no LED's lit. Once a certain level is reached that associated LED is lit. If a higher G-force or frequency is met the next stage is lit. The order is Red low, Yellow mid range, Green optimal. A label 8 shows the LED set showing G force. A label 9 shows speed/frequency. Additional components may be added in the future for additional features such as vibration offset motor which is activated when optimum speed and or frequency is reached. Also a wireless system for headset audio feedback via blue tooth communications can be employed as feedback of optimum speed and frequency for example. Other embodiments include the Wrist Band Motion Analyzer to be water proof by employing a water proofing seal or system to at least five meters through use of a sealing gasket.

While the present invention has been described above in terms of specific embodiments, it is to be understood that the invention is not limited to these disclosed embodiments.

Upon reading the teachings of this disclosure many modifications and other embodiments of the invention will come to mind of those skilled in the art to which this invention pertains, and which are intended to be and are covered by both this disclosure and the appended claims. It is indeed intended that the scope of the invention should be determined by proper interpretation and construction of the appended claims and their legal equivalents, as understood by those of skill in the art relying upon the disclosure in this specification and the attached drawings.

The invention claimed is:

1. A Wrist Band Motion Analyzer comprising
a housing having a wrist band for securing the wrist band motion analyzer to a user's wrist, lens, a push button, a microcontroller, an accelerometer, at least two light emitting diodes configured to emit red, yellow, and/or green light, resistors, capacitors and at least one battery;
wherein the wrist band motion analyzer is configured to be activated when the user presses the push button at which time the microcontroller turns on the accelerometer and accumulates raw data from the accelerometer in real time, the microcontroller is configured to collect and process the raw data for G-force and frequency and compares the calculated G-force and frequency data to a stored value to determine optimum force and frequency for the user, wherein the microcontroller includes a Fast Fourier Transform (FFT) which is configured to perform a calculation based on calculated voltage data from the accelerometer in a stored array and perform a level conversion to detect the frequency of motion of the wrist band motion analyzer, then the calculated value of frequency is compared against known values at which point if the calculated frequency is optimum the at least two light emitting diodes will emit green light for frequency, and if the calculated frequency is in the middle of the range compared to the known stored values but not optimum yellow light will be emitted from the at least two light emitting diodes for frequency and if the calculated frequency is in the low range compared to the known stored values red light will be emitted from the at least two light emitting diodes for frequency; wherein the microcontroller is further configured to compute peak detection for the calculated G-force which is also stored and compared against the stored known optimum values and if the optimum value is present the at least two light emitting diodes will emit green light for force and if the calculated G-force is in the middle range of the stored known values but not optimum the at least two light emitting diodes will emit yellow light for force and if the calculated G-force value is in the low range compared to the known stored values red light will be emitted from the at least two light emitting diodes for force;
wherein the wrist band motion analyzer is configured to assists in achieving an ejaculating orgasm in women by giving feedback to the user wearing the wrist band motion analyzer for proper force and frequency of the user's wrist/hand/finger motion on a subject's G spot.

2. The Wrist Band Motion Analyzer of claim 1 further comprises seals for waterproofing the wrist band motion analyzer to at least five meters.

3. The Wrist Band Motion Analyzer of claim 1; wherein the at least two light emitting diodes includes two single light emitting diodes used for emitting all three colors red, yellow and green.

4. The Wrist Band Motion Analyzer of claim 1; wherein the wrist band motion analyzer is configured to function as a wrist watch and has a secret mode that activates the microcontroller, accelerometer and at least two light emitting diodes.

5. The Wrist Band Motion Analyzer of claim 1 further comprises an audible feedback system.

6. The Wrist Band Motion Analyzer of claim 1 further comprises a blue tooth feedback system.

7. The Wrist Band Motion Analyzer of claim 1; wherein the wrist band motion analyzer is configured to enter a low power mode to extend battery life.

8. The Wrist Band Motion Analyzer of claim 1; wherein the at least two light emitting diodes includes two sets of light emitting diodes, a first set of light emitting diodes for emitting light based on the G-force data and a second set of light emitting diodes for emitting light based on the frequency data.

\* \* \* \* \*